US00PP31830P2

(12) United States Plant Patent
Wood

(10) Patent No.: US PP31,830 P2
(45) Date of Patent: Jun. 2, 2020

(54) ***SYRINGA* 'SMSDTL'**

(50) Latin Name: *Syringa debelderi*
Varietal Denomination: SMSDTL

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/501,875

(22) Filed: Jun. 19, 2019

(51) Int. Cl.
*A01H 5/00* (2018.01)

(52) U.S. Cl.
USPC ..... Plt./248

(58) Field of Classification Search
USPC ..... Plt./248
CPC ..... A01H 5/00
See application file for complete search history.

*Primary Examiner* — Annette H Para
(74) *Attorney, Agent, or Firm* — Cassandra Bright

(57) ABSTRACT

A new and distinct *Syringa* cultivar named 'SMSDTL' is disclosed, characterized by a distinctive compact, dwarf habit. Plants produce attractive foliage and lavender flowers. The new variety is a *Syringa* normally produced as an outdoor garden or container plant.

2 Drawing Sheets

Latin name of the genus and species: *Syringa debelderi*.
Variety denomination: 'SMSDTL'.

BACKGROUND OF THE INVENTION

The present invention comprises a new and distinct variety of *Syringa*, hereinafter referred to by the cultivar name 'SMSDTL'. This new *Syringa* was developed through a breeding program in Grand Haven, Mich. The objective of the breeding program was to develop new *Syringa* colors and forms. 'SMSDTL' is an internal advanced selection from an in-house breeding program. The seed parent is an unnamed, unpatented selection of *Syringa pubescens* subsp. *patula*. The pollen parent is unidentified as the new variety was produced through an open pollination breeding program. The open pollination resulting in the new variety was made in Spring of 2005. Selection of the new variety was made in May 2007.

The first asexual propagation of 'SMSDTL' was carried out in June 2007 by softwood cuttings at a commercial nursery in Grand Haven, Mich. 'SMSDTL' has been found to retain its distinctive characteristics through successive asexual propagations. Multiple generations have been propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. More dwarf than other *Syringa* varieties.
2. Compact habit.
3. Attractive foliage.
4. Lavender flowers.

COMPARISON WITH THE PARENT VARIETIES

'SMSDTL' is similar to the seed parent, in most horticultural characteristics. 'SMSDTL' however differs in the following:

1. The new variety is a more dwarf plant than the seed parent.
2. The new variety has light lavender flowers, while the seed parent has more purple flowers.

COMMERCIAL COMPARISON

'SMSDTL' is similar to the unpatented commercial variety *Syringa patula* 'Miss Kim', in most horticultural characteristics. 'SMSDTL' however differs in the following:

1. Plants of the new variety are more dwarf, while this comparator is a larger, rangier plant.
2. New variety has light lavender flowers, while this comparator has lavender blue flowers.

DESCRIPTION OF THE PHOTOGRAPHS

This new *Syringa* is illustrated by the accompanying photographs which show the plant's form, foliage and inflorescences. The colors shown are as true as can be reasonably obtained by conventional photographic procedures. Plants were grown in Grand Haven, Mich.

Figure 1:
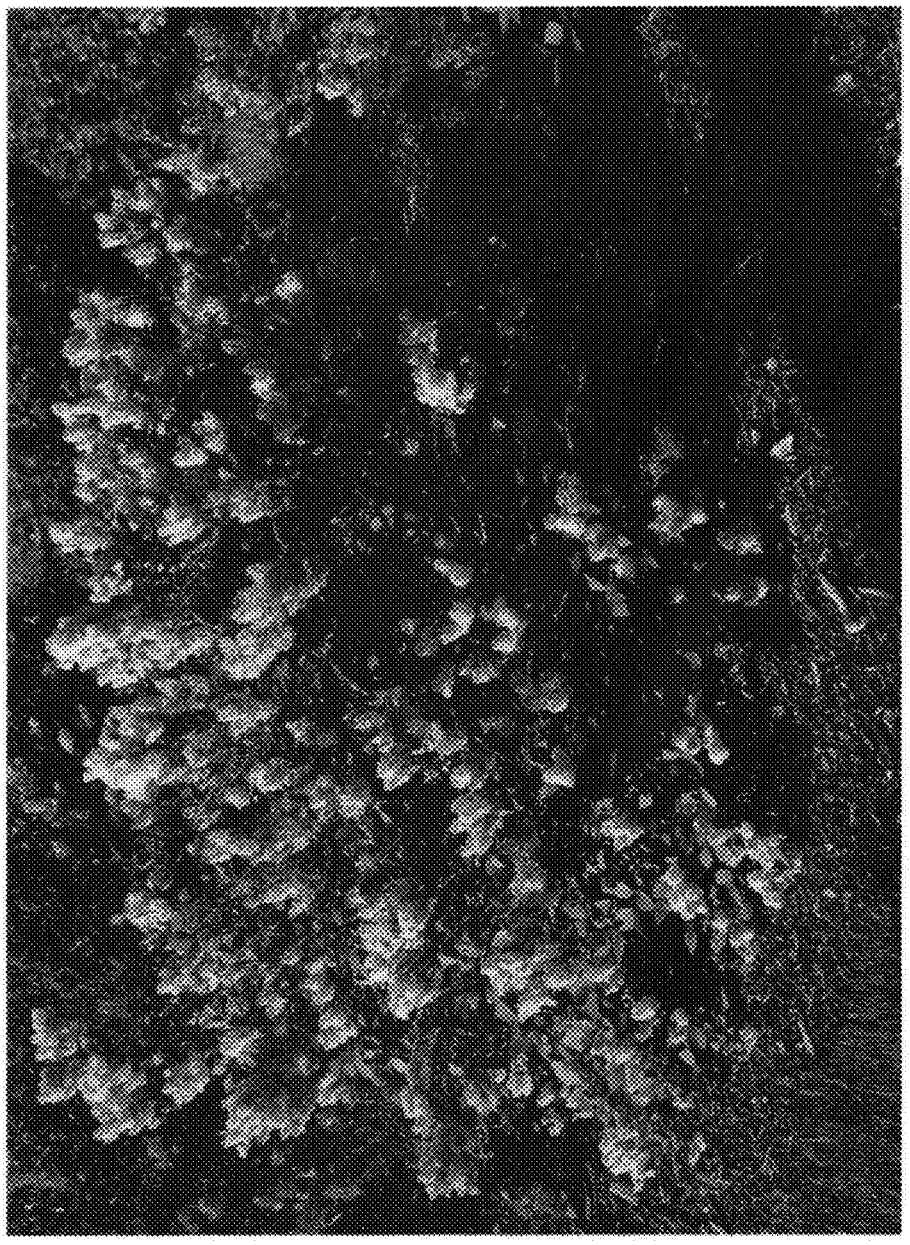

FIG. 1. Shows a flowering plant of 'SMSDTL' in the ground at approximately 3 years old during Summer.

Figure 2:
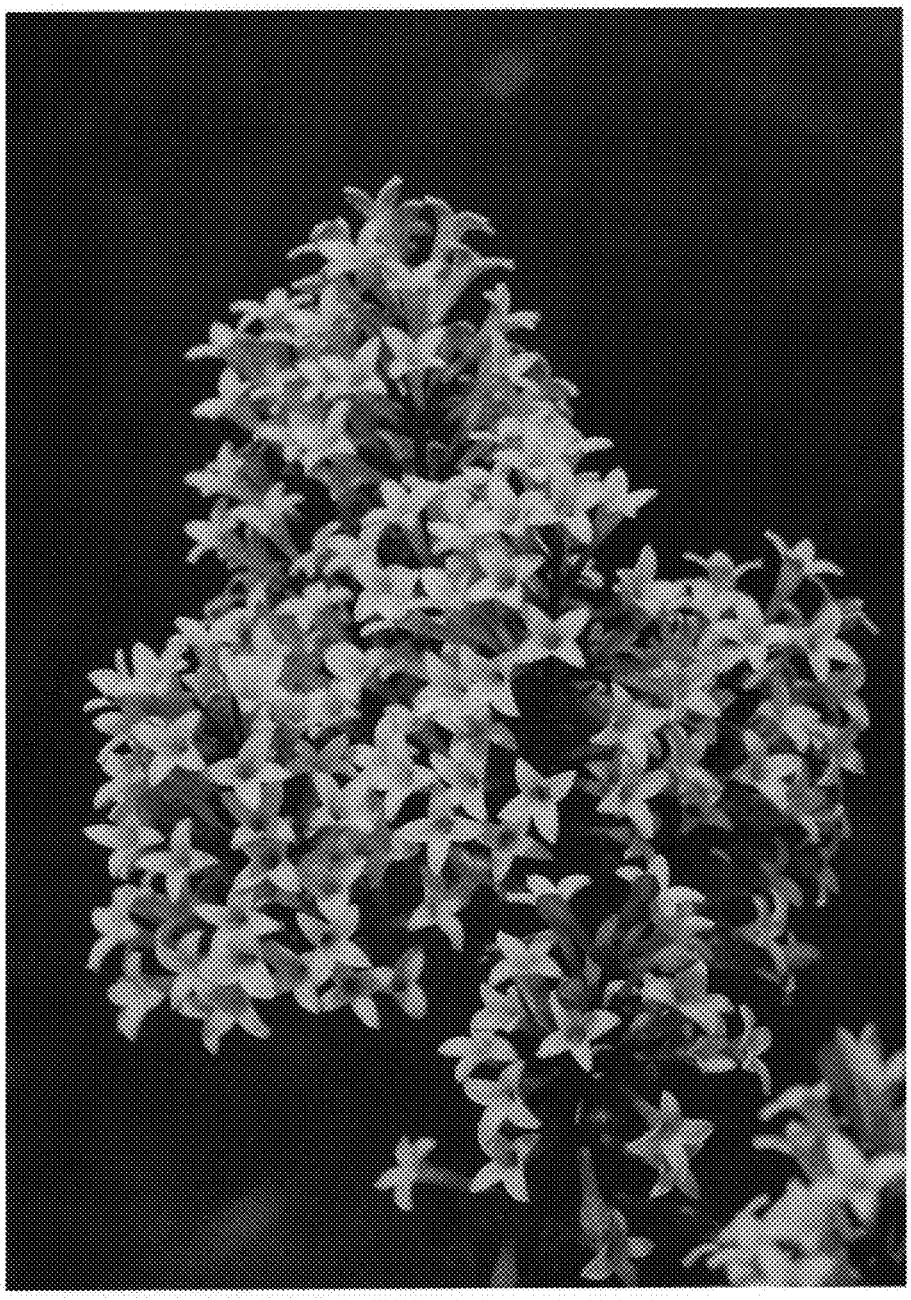

FIG. 2. Shows a close-up view of the inflorescence.

DESCRIPTION OF THE NEW CULTIVAR

In the following description, color references are made to The Royal Horticultural Society Colour Chart 2015 except where general terms of ordinary dictionary significance are used. The following observations and measurements describe 'SMSDTL' plants grown in a poly-greenhouse during Summer, in Grand Haven, Mich. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Syringa debelderi* 'SMSDTL'.
Propagation:
Typical method: Softwood cuttings.
Time to initiate rooting: About 20 days at approximately 18° C. to 27° C.
Time to produce a rooted young plant: About 3 months at approximately 18° C. to 27° C.
Root description: Dense, free branching, thin, fibrous. Colored white, not accurately measured with an R.H.S. chart.
Plant description:
*Age of plant described.*—2 to 3 years in a 3 gallon container.
*Plant shape.*—Perennial shrub. Rounded.
*Growth habit.*—Upwards and outwards.
*Height.*—69 cm.
*Width.*—95 cm.
*Growth rate.*—Good.
*Plant vigor.*—Moderate.
Branches:
*Branching habit.*—Upwards and outwards.
*Lateral branch quantity.*—50.
*Lateral branch length.*—56 cm.
*Lateral branch diameter.*—5 mm.
*Branch aspect.*—Upwards.
*Branch strength.*—Good.
*Branch color.*—New growth: RHS Green 143B. Old growth: Close to RHS Greyed-Green 197A.
*Internode length.*—3 cm.
Foliage:
Leaves:
*Arrangement.*—Opposite.
*Length.*—4 cm.
*Width.*—5.5 cm.
*Shape.*—Ovate.
*Apex.*—Acute.
*Base.*—Obtuse.
*Margin.*—Entire.
*Texture upper surface.*—Soft.
*Texture lower surface.*—Soft, distinct veins.
*Color.*—Immature: Upper: RHS Yellow-Green 144A. Lower: RHS Yellow-Green 144A. Mature: Upper: RHS Green 137A. Lower: RHS Green 138A.
Venation:
*Pattern.*—Pinnate.
*Color.*—Upper: RHS Yellow-Green 144C. Lower: RHS Yellow-Green 144C.
Petiole:
*Length.*—1.5 cm.
*Width.*—2 mm.
*Texture.*—Smooth.
*Color.*—Upper side: RHS Yellow-Green 144C. Under side: RHS Yellow-Green 144C.
Inflorescence:
*Description.*—Bunches of panicles.
*Flowering season.*—Spring.
*Fragrance.*—Moderately strong, floral.
*Inflorescence type.*—Panicles.
*Number of flowers per inflorescence.*—75-100.
*Inflorescence height.*—12.5 cm.
*Inflorescence diameter.*—4.5 cm.
Flowers:
*Flower type.*—Funnelform/salverform.
*Flowering habit.*—Terminal and axial on the panicles.
*Flowers per lateral stem.*—Over 1000.
*Flower diameter.*—5 mm.
*Flower depth.*—5 mm.
*Flower throat diameter.*—2 mm.
*Flower tube diameter* (*base*).—1 mm.
*Flower tube length.*—4 mm.
*Flower angle.*—Upright, outward and drooping.
*Persistence.*—Self-Cleaning.
Flower bud:
*Buds per lateral stem.*—Over 1000.
*Length.*—6 mm.
*Diameter.*—2 mm.
*Shape.*—Obovate.
*Color.*—RHS White N155A.
Petals:
*Number.*—4.
*Arrangement.*—Rotate.
*Length.*—1 mm.
*Width.*—1 mm.
*Shape.*—Ovate.
*Apex.*—Acute, slightly recurved.
*Margin.*—Entire.
*Texture.*—Soft, smooth, delicate.
*Throat texture.*—Smooth.
*Tube texture.*—Smooth.
*Color.*—Immature upper surface: RHS Red-Purple 69D. Immature lower surface: RHS Purple 75A and Yellow 10A. Mature upper surface: RHS White NN155C. Mature lower surface: RHS White NN155C.
*Flower tube* (*interior*).—Mix of RHS Purple 75A and White NN155C.
*Flower throat* (*exterior*).—RHS White NN155C.
Sepals: Inconspicuous and extremely reduced. Too minute (less than 1 mm by 1 mm in size) for accurate measurement.
Peduncle:
*Length.*—5 cm.
*Width.*—2 mm.
*Color.*—RHS Green 138A.
*Texture.*—Smooth.
*Angle.*—Upright/outward.
*Strength.*—Good.
Pedicels:
*Length.*—3-5 mm.
*Diameter.*—1 mm.
*Texture.*—Smooth, pubescent.
*Color.*—RHS Green 138A.
*Strength.*—Good.
*Angle.*—Upright/outward.
Reproductive organs:
Gynoecium:
*Pistil number.*—1.
*Pistil length.*—3 mm.
*Stigma shape.*—Oblong to rounded.
*Stigma color.*—Close to RHS White 155A.
*Style length.*—About 2 mm.
*Style color.*—Close to RHS White 155A.
Androecium:
*Stamen number.*—2.
*Filament length.*—1.5 mm.
*Filament color.*—RHS White NN155C.
*Anther shape.*—Oblong.
*Anther length.*—2 mm.
*Anther color.*—RHS Grey 201A.

*Amount of pollen*.—Some.
*Pollen color*.—RHS Green-Yellow 1A.

OTHER CHARACTERISTICS

Fruit: Not observed to date.
Disease and insect resistance: No significant disease or pest resistance nor susceptibility have been observed.
Temperature range: Observed to tolerate temperatures between −33° C. and 36° C.

What is claimed is:

1. A new and distinct *Syringa* named 'SMSDTL' as illustrated and described herein.

* * * * *